(12) United States Patent
Hanselmann et al.

(10) Patent No.: US 9,394,238 B2
(45) Date of Patent: *Jul. 19, 2016

(54) PROCESS FOR THE PRODUCTION OF CARNITINE FROM β-LACTONES

(71) Applicant: Lonza Ltd., Basel (CH)

(72) Inventors: Paul Hanselmann, Brig-Glis (CH); Ellen Klegraf, Brig-Glis (CH)

(73) Assignee: LONZA LTD., Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/521,700

(22) Filed: Oct. 23, 2014

(65) Prior Publication Data

US 2015/0126775 A1    May 7, 2015

Related U.S. Application Data

(63) Continuation of application No. 13/187,177, filed on Jul. 20, 2011, now abandoned.

(60) Provisional application No. 61/366,390, filed on Jul. 21, 2010, provisional application No. 61/425,848, filed on Dec. 22, 2010.

(30) Foreign Application Priority Data

Jul. 21, 2010  (EP) .................... 10007568
Dec. 22, 2010 (EP) .................... 10015942

(51) Int. Cl.
  *C07C 229/12*   (2006.01)
  *C07C 229/22*   (2006.01)
  *C07C 227/08*   (2006.01)
  *C07C 227/40*   (2006.01)
  *C07C 227/42*   (2006.01)
  *C07D 305/12*   (2006.01)

(52) U.S. Cl.
  CPC ............. *C07C 229/22* (2013.01); *C07C 227/08* (2013.01); *C07C 227/40* (2013.01); *C07C 227/42* (2013.01); *C07D 305/12* (2013.01)

(58) Field of Classification Search
  None
  See application file for complete search history.

(56) References Cited

U.S. PATENT DOCUMENTS

| 3,468,937 | A  | 9/1969  | Strack et al. |
| 5,473,104 | A  | 12/1995 | McCarthy |
| 6,040,465 | A  | 3/2000  | Miyano et al. |
| 8,563,752 | B2 | 10/2013 | Hanselmann et al. |

FOREIGN PATENT DOCUMENTS

| CH | 680588 A5 | 9/1992 |
| CH | WO2009062731 A1 | 5/2009 |
| CN | 1727328 | 2/2006 |
| JP | H10251241 A | 9/1998 |
| JP | 2009102258 | 5/2009 |
| JP | 2010143857 | 7/2010 |
| JP | 2013520004 | 9/2013 |

OTHER PUBLICATIONS

Calter et al., "Catalytic, Asymmetric Dimerization of Methylketene", Journal of Organic Chemistry, vol. 61, pp. 8006-8007; 1996.
Mondal et al., "Phospine-Catalyzed Asymmetric Synthesis of Beta-Lactones from Arylketoketones and Aromatic Aldehydes", Organic Letters, vol. 12, No. 8, pp. 1664-1667; 2010.
Shen et al., "Catalytic Asymmetric Assembly of Stereodefined Propionate Units: An Enantioselective Total Synthesis of (−)-Pironetin", J. Am. Chem. Soc., vol. 128, pp. 7436-7439; 2006.
Zhu et al., "Cinchona Alkaloid-Lewis Acid Catalyst Systems for Enantioselective Ketene-Aldehyde Cycloadditions", J Am. Chem. Soc., vol. 126, pp. 5352-5353.
Song et al., "New Method for the Preparation of (R)-Carnitine", Elsevier Science Ltd., Elsevier Science Ltd., 1995, 1063-1066, vol. 6, No. 5.
Lin et al., "A Lewis Acid-Lewis Base Bifunctional Catalyst from a New Mixed Ligand", American Chemical Society, 2007, 567-570, vol. 9, No. 4.
Wilson et al., "Asymmetric Synthesis of Highly Substituted Beta-Lactones by Nucleophile-Catalyzed [2+2] Cycloadditions of Disubstituted Ketenes with Aldehydes", Wiley-VCH Verlag, GmbH & Co., 2004, 6518-6520.
Chidara et al., "Reaction Rate Acceleration Enabled by Tethered Lewis Acid-Lewis Base Bifunctional Catalysis: A Catalytic, Enantioselective [2+2] Ketene Aldehyde Cycloaddition Reaction", Synlett, 2009, 1675-1679.

*Primary Examiner* — Yevegeny Valenrod
(74) *Attorney, Agent, or Firm* — Hoffman & Baron, LLP

(57) ABSTRACT

The invention relates to a method for the production of L-carnitine, wherein a β-lactone, which is a 4-(halomethyl)oxetane-2-one, is converted into carnitine with trimethylamine (TMA), wherein the β-lactone is not subjected to a basic hydrolysis step before being contacted with the trimethylamine. The invention also relates to a carnitine having a unique impurity profile.

19 Claims, No Drawings

PROCESS FOR THE PRODUCTION OF CARNITINE FROM β-LACTONES

CROSS-REFERENCE TO RELATED APPLICATION

This application claims the benefit of priority from U.S. Non-Provisional patent application Ser. No. 13/187,177 filed Jul. 20, 2011, which claims the benefit of priority from European Patent Application No. 10007568.8 filed Jul. 21, 2010, European Patent Application No. 10015942.5 filed Dec. 22, 2010, U.S. Provisional Patent Application No. 61/366,390 filed Jul. 21, 2010 and U.S. Provisional Patent Application No. 61/425,848 filed Dec. 22, 2010, which are incorporated herein by reference.

The invention relates to methods for the production of L-carnitine as well as L-carnitine with a unique impurity profile.

BACKGROUND OF THE INVENTION

Carnitine (vitamin Bt; 3-hydroxy-4-trimethylammoniobutanoate) is a quaternary ammonium compound biosynthesized from the amino acids lysine and methionine. In living cells, it is required for the transport of fatty acids from the cytosol into the mitochondria during the breakdown of lipids for the generation of metabolic energy. It is used as a nutritional supplement. Carnitine exists in two stereoisomers. The biologically active form is L-carnitine, whilst its enantiomer, D-carnitine, is biologically inactive. When producing L-carnitine in an industrial process, it is desirable to produce the biologically active L-form in high purity.

Various methods were described for the industrial production of L-carnitine. Microbiological processes are known, in which L-carnitine is produced directly by bacteria. In other processes, a racemate is produced by organic synthesis and separated subsequently into enantiomers.

Further, attempts have been made to synthesize L-carnitine directly from chiral precursors. A group of potential precursors are chiral cyclic lactones. Since methods for obtaining chiral lactones are known in principle, L-carnitine is available upon hydrolysis of the lactone ring.

U.S. Pat. No. 5,473,104 discloses a process for the preparation of L-carnitine from (S)-3-hydroxybutyrolactone. The process is a two-step process, wherein in a first step (S)-3-hydroxybutyrolactone is converted into the corresponding hydroxy-activated lactone, whilst maintaining the ring structure. In a second step, the ring of the activated lactone is opened and the trimethylammonium group is introduced with trimethylamine. Altogether, the reaction is relatively complicated because it requires the activation of an intermediate with harsh chemicals.

CH 680 588 A5 discloses a process for producing L-carnitine from a β-lactone precursor, wherein a chiral 2-oxetanone is converted into L-carnitine in a two-step process. In a first step, 4-(chloromethyl)-2-oxetanone is subjected to a hydrolysis step, in which the ring is opened and 4-chloro-3-hydroxybutyric acid is obtained. In a subsequent step, the acid is converted into L-carnitine with trimethylamine. However, the reaction is a two-step reaction, and thus relatively labor- and time-consuming. Further, reactions in multiple steps are generally more susceptibly to variations and associated with a relatively low product yield.

Since chiral L-carnitine is an important industrial product, it would be desirable to provide alternative efficient processes for its production. Specifically, it would be desirable to provide processes for the production of L-carnitine in a relatively simple manner and at a high yield.

Problem Underlying the Invention

The problem underlying the invention is to provide a method for producing L-carnitine, which overcomes the above-mentioned drawbacks. Specifically, the problem is to provide an efficient and simple process for the production of L-carnitine.

The total yield as well as the chiral yield shall be high. Further, the necessary chemicals shall be readily available and should not be too expensive. Specifically, the use of expensive catalysts comprising precious metals, such as platinum, shall be avoided.

The number of process steps shall be relatively low and the process shall not require complicated apparatuses. Overall, the process shall have a high be atom economy and shall be cost and labour efficient.

DESCRIPTION OF THE INVENTION

Surprisingly, the problem underlying the invention is solved by the process according to the claims. Further inventive embodiments are disclosed throughout the description.

Subject of the invention is a process for the production of carnitine, wherein a β-lactone, which is a 4-(halomethyl) oxetane-2-one, is converted into carnitine with trimethylamine (TMA), wherein the β-lactone is not subjected to a hydrolysis step before being contacted with the trimethylamine. The hydrolysis step, can be any hydrolysis step, for example under acidic or basic conditions, which opens the β-lactone ring. However, esters are commonly hydrolysed under basic conditions in a basic hydrolysis.

In specific embodiments of the invention, the β-lactone is 4-(chloromethyl)oxetane-2-one, 4-(bromomethyl)oxetane-2-one or 4-(iodomethyl)oxetane-2-one. The use of 4-(chloromethyl)oxetane-2-one is preferred. Preferably, the β-lactone is a chiral β-lactone and the carnitine is L-carnitine. L-carnitine is available when the (R)-β-lactone is used. According to the invention, the β-lactone ring is opened in a basic hydrolysis reaction and the halogen atom is substituted by a trimethylamine group in a nucleophilic substitution reaction. This is achieved in a novel one-step pathway. The halogenated β-lactone can be converted into L-carnitine without a hydrolysis before the TMA addition. The TMA can be brought into contact with the β-lactone together with an additional base for basic hydrolysis, or the reaction can be carried out without an addition of an additional base at all, or an additional base for basic hydrolysis might be added after bringing the β-lactone in contact with the TMA. Scheme 1 below shows an exemplified inventive reaction for the production of carnitine, in which a chlorinated β-lactone is brought into contact with a combination of TMA and aqueous NaOH as a hydrolytic base.

Scheme 1: Synthesis of L-carnitine by cleavage of a cyclic β-lactone.

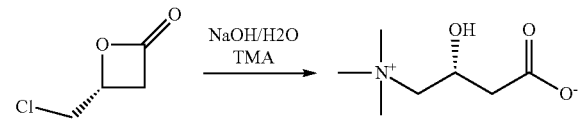

The prior art requires a two step pathway, which is disclosed in CH 680 588 A5. In a first step, the halogenated β-lactone is hydrolysed, usually under basic conditions, to obtain 4-halo-3-hydroxybutyric acid. In a second step, the acid is converted into L-carnitine with TMA. This two-step approach was used in the art, because in a one-step reaction numerous side reactions were observed or expected, which concur with the desired reaction and inhibit carnitine formation or at least strongly reduce the yield and efficiency.

The side reaction and side products, which are observed and would be expected when carrying out the basic hydrolysis and the halogen substitution with TMA in one single step, are summarized in scheme 2 below. Scheme 2 illustrates all the side reactions which occur, or could occur in theory, when 4-(chloromethyl)oxetane-2-one is reacted with NaOH and TMA. Scheme 2 thus shows the reaction pathways, which are observed in one single reaction batch. Some of the products, such as the lactone 13, may be transient intermediates. Other compounds, especially hydroxycrotonic acid 8, crotonobetaine 10 and the cyclic lactone 6 and furanone 7 are competitive end products. When analyzing the product mixture of a reaction, it was found that the main impurities within this synthesis are hydroxycrotonic acid 8 and crotonobetaine 10. In principle, the 4-(chloromethyl)oxetane-2-one 4 can enter two reaction pathways in the presence of NaOH and TMA.

The first pathway starts with basic hydrolysis of the beta lactone 4 to chloro hydroxybutyric acid 5, which can cyclize giving the hydroxybutyrolactone 6 or after elimination of water forming the furanone 7. Formation of hydroxybutyric acid 8 proceeds via intermediate 9, which results from elimination of water from compound 5. Additionally, furanone 7 can also be formed by cyclization reaction of intermediate 9. Crotonobetaine 10 can be obtained by either L-carnitine 1 eliminating water or by compound 9 reacting undergoing nucleophilic substitution of the chloride by trimethylamine. Also epoxy acid 11 can be formed from L-carnitine 1 or 5 by intramolecular nucleophilic substitution of chloride or ammonium by the alcohol group. As both the primary alkylhalogenide in 5 and the ammonium group in L-carnitine 1 represent good leaving groups, a side reaction is their nucleophilic substitution by hydroxide giving the diol 12. The second pathway starts with the amination of the chloro-β-lactone 4 to intermediate 13, which is hydrolyzed with sodium hydroxide to L-carnitine 1. Especially by having not the right reaction conditions, L-carnitine 1 can also undergo further reactions such as cyclization and elimination giving side products 6 and 7 or the above mentioned elimination yielding compound 10.

Scheme 2: Potential reactions of 4-(chloromethyl)oxetane-2-one upon contact with a combination of NaOH and TMA. According to the invention, side reactions can be suppressed and carnitine 1 is obtained as the main product.

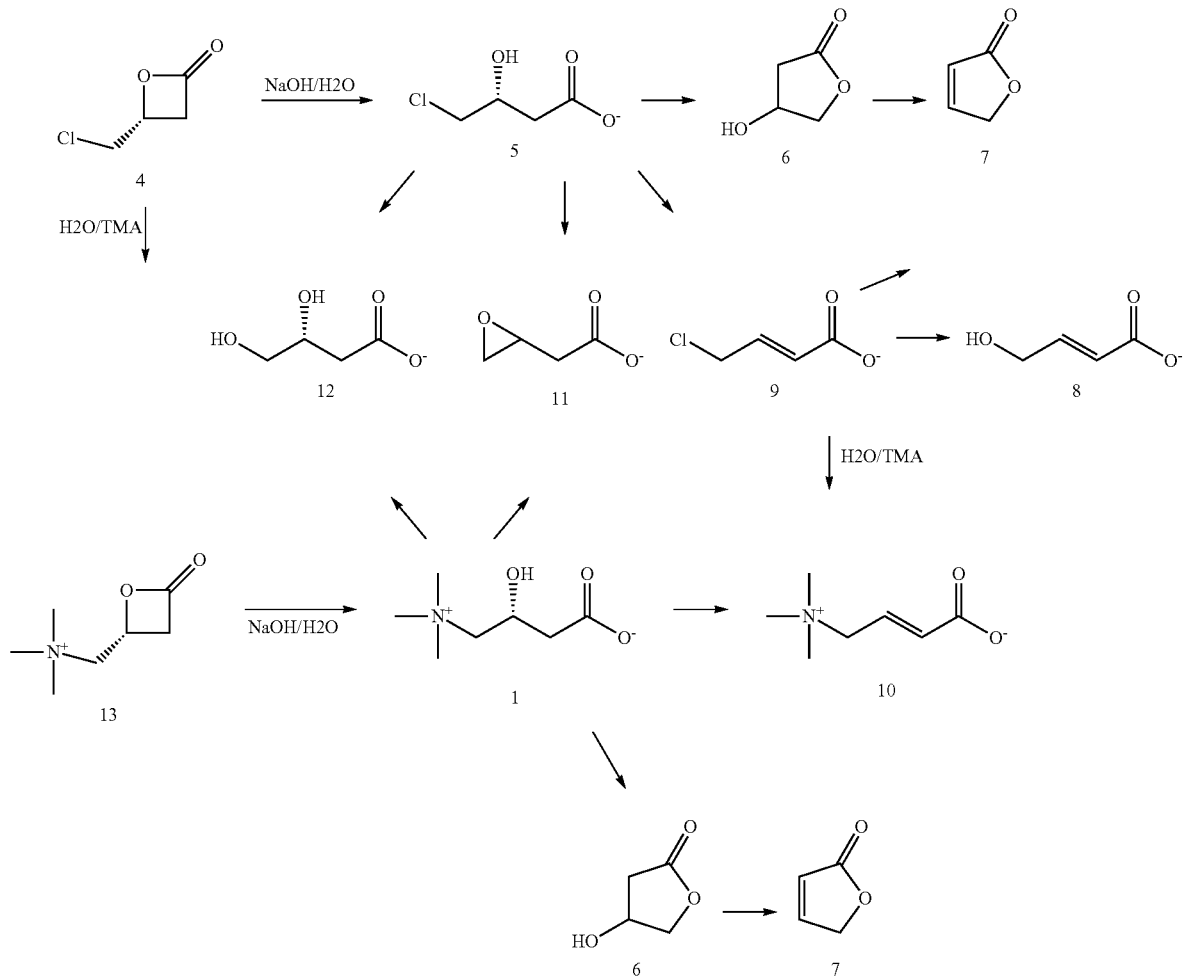

In summary, scheme 2 shows that a multitude of reactions occurs, or would at least be expected, when carrying out a basic hydrolysis of the β-lactone and the nucleophilic substitution reaction with TMA at the same time in one batch. The skilled person would not have expected that both reactions could be carried out efficiently at the same time in the same batch, i. e. that the addition of the TMA and an additional base together would yield carnitine in high amounts. In contrast, he would have expected that especially hydroxycrotonic acid 8 and crotonobetaine 10 and cyclic lactones 6 and 7 would be obtained at significant high yields. Indeed, in initial experiments it was found that the addition of a combination of NaOH with TMA to the β-lactone precursor did not yield L-carnitine in relevant amounts, but various side products as shown in scheme 2 instead. Surprisingly, it was found in further experiments that upon variation of the process conditions (as outlined further below and as shown in the examples), a selective shift of the overall reactions towards L-carnitine production in high amounts occurred. It is unusual that two different process steps can be combined in one single step in a reaction, which is as complicated as outlined above and as illustrated by scheme 2.

According to the invention, the basic hydrolysis (ring opening reaction) and reaction with trimethylamine (TMA) are carried out in one process step. An additional base different from TMA may be added for the basic hydrolysis. Alternatively, the conditions can be adjusted such that the base TMA itself triggers the basic hydrolysis. In this embodiment, it is not necessary to add an additional base.

In a preferred embodiment, an additional base is added, which is preferably a metal hydroxide. In this embodiment, the β-lactone should be brought into contact with the additional base and with the trimethylamine essentially at the same time. Preferably, the additional base and the trimethylamine are added at the same time, preferably in the form of a mixture, for example a solution or suspension, of metal hydroxide and trimethylamine, or by adding the metal hydroxide and passing gaseous TMA through the reaction mixture.

When added at the same time, the metal hydroxide triggers the basic hydrolysis and the trimethylamine reacts with the β-lactone by replacing the halogen atom in a nucleophilic substitution. The term "essentially" expresses, that it is not necessary that both components are added precisely at the same time. In principle, both components can be added to the reaction mixture one after the other within a short time span. However, the metal hydroxide should be added before the trimethylamine has considerably reacted in a nucleophilic substitution, or vice versa the trimethylamine should be added before the metal hydroxide has considerably reacted in the ring opening reaction. Thus, both components also can be added one after the other, as long as it is ensured that both reactions are carried out simultaneously, or at least that 90% or 95% of the reactions are carried out simultaneously. Especially when it is ensured that the reactions do not proceed or proceeds slowly, for example due to a low temperature, it is possible to add one component first and the second component subsequently. When adding the metal hydroxide before the TMA, it should be ensured that no basic hydrolysis occurs before the TMA is added, or that only a neglectable basic hydrolysis occurs, for example of less than 5% of the total β-lactone.

In a preferred embodiment of the invention, the basic hydrolysis is carried out by adding a metal hydroxide, preferably sodium hydroxide. In principle, the basic hydrolysis is an ester hydrolysis reaction and reactants know in the art can be used for this step. Thus the basic hydrolysis can also be carried out with other bases, for example potassium hydroxide, lithium hydroxide, calcium hydroxide or magnesium hydroxide.

Preferably, the solvent used according to the invention is water. Alternatively, the reaction can be carried out in a two-phase system comprising water and an organic solvent. In another embodiment, the reaction may be carried out without water in an organic solvent, for example an alcohol, such as ethanol. In this embodiment, a base is added which is free of water or essentially free of water.

In a preferred embodiment of the invention, the amount of the additional base, especially the metal hydroxide, is 1.1 to 1.6 equivalents, preferably 1.2 to 1.4 equivalents, based on the initial amount of β-lactone. As outlined above, the basic hydrolysis is an ester hydrolysis reaction, which is in principle well known in the art. However, the basic hydrolysis of an ester according to the state of the art is commonly carried out with a high surplus of a base, for example with a metal hydroxide, such as sodium hydroxide, in a surplus of about 3 to 4 equivalents. Surprisingly, it was found according to the invention that the yield of carnitine is low when such a high stoichiometric excess of a base is added. According to the invention, it was found that a low surplus of a base is advantageous for selectively obtaining carnitine and for suppressing the formation of side products.

In a preferred embodiment of the invention, the reaction is carried out at a temperature between −20° C. and 40° C., preferably between 0° C. and 25° C., preferably at about 0° C. and/or about 25° C. In a preferred embodiment, the temperature is increased during the process, for example from about 0° C. to about 25° C. In a preferred embodiment, the reaction is carried out at normal pressure. Thus, energy can be saved, which is important for industrial scale production.

In a preferred embodiment of the invention, the β-lactone is brought into contact with an aqueous solution comprising a metal hydroxide and TMA. The concentration of the metal hydroxide in the aqueous solution may be between 1 and 20 wt. %, preferably between 2 and 10 wt. %. The concentration of the TMA in the aqueous solution may be between 2 and 15 wt. %, preferably between 3 and 10 wt. %. The β-lactone may be provided in pure form or in an aqueous solution, for example at a concentration between 1 and 80%, preferably between 5 and 50%. It is preferred that the reaction of the β-lactone with TMA and metal hydroxide in aqueous solution is carried out at room temperature or between 0 and 40° C. The reaction time may be between 20 minutes and 5 hours, preferably between 30 minutes and 3 hours. In this embodiment, enhanced pressure is not necessary. Thus, the reaction can be carried out at low temperatures and without enhanced pressure and is energy-efficient.

Preferably, the β-lactone is added to the aqueous solution comprising TMA and a metal hydroxide. The β-lactone or β-lactone comprising aqueous solution may be added slowly, for example over a time span of 10 minutes to 4 hours, preferably dropwise.

In another preferred embodiment of the invention, a solution of the β-lactone in an organic solvent is provided and mixed with an aqueous solution comprising TMA and a metal hydroxide. In this embodiment, the reaction is proceeds in a biphasic system. Preferred organic solvents are tert-butylmethylether (MTBE), dichloromethane (DCM), dichloroethylene (DCE), chloroform, chlorobenzene or toluene. However, other solvents are also appropriate which form a separate organic phase and which do not interfere with the reaction. In theory, chlorinated solvents might react with TMA. Although this was not observed, it would be acceptable, if the production of carnitine is not severely inhibited. The concentration of the β-lactone in the organic solvent may be between 2 and 50 wt. %, preferably between 5 and 20 wt. %. In this embodiment, a surplus of about 1 to 4 equivalents, preferably 1.1 to 4 equivalents, more preferably between 2 and 3 equivalents of TMA, may be used. The two-phase reaction can be carried out at low temperatures, for example between −20 and 40° C., or between 0 and 25° C., preferably at 0° C.

In a preferred embodiment of the invention, the TMA is recycled during the process. Since TMA is available in gaseous form, it can be led through the reaction fluid, collected and recycled. In the reaction medium, dissolved TMA can be separated from the mixture after reaction is finished (eg by distillation) and reintroduced in the process. Preferably, the TMA is reintroduced into the reaction pathway in a cyclic process. TMA is commercially available in the form of a pure gas (Fluka Chemicals) or in the form of an aqueous solution of 10 to 40 wt. %. The amount of TMA in the reaction mixture may be between 1 and 3 equivalents, preferably between 1 and 2.5 equivalents. However, the amount and excess of TMA is less critical than the amount of metal hydroxide, because it can be recycled during the reaction and reintroduced into the reaction chamber.

In a preferred embodiment of the invention, the reaction mixture consists of the β-lactone, water, metal hydroxide and TMA. Additional components may be present at a level below 1% or below 2%. When only using this composition, the reaction mixture is simple and side reactions are minimized.

In a specific embodiment of the invention, the basic hydrolysis is mediated by the TMA and no additional base is added for basic hydrolysis. Preferably, this reaction is carried out at enhanced pressure and/or at least in part at enhanced temperature. In a specific embodiment, the solvent is ethanol and the reaction intermediate product is an ethylester of carnitine, which is subsequently hydrolyzed to carnitine. In a specific embodiment of the invention, the solvent is an alcohol and the reaction product is an ester, which is subsequently subjected to a basic hydrolysis.

In this embodiment without an additional base, it is preferred to carry out the reaction at enhanced pressure, preferably in an autoclave. For example, the pressure may be between 2 and 200 bar, especially between 5 and 150 bar or between 10 and 100 bar. The application of enhanced pressure is preferred when the reaction is carried out without an additional base for basic hydrolysis. The hydrolysis reaction with the weak base TMA, which is gaseous, is promoted upon increased pressure.

In this embodiment without an additional base and at enhanced pressure, it is preferred to carry out the reaction at least in part at enhanced temperature, for example between 50° C. and 120° C., more preferably between 80° C. and 10° C. The initial temperature may be below 0° C. and raised during the reaction.

In a preferred embodiment of the invention, the yield of L-carnitine is at least 75%, more preferably at least 80%, most preferably at least 85 or at least 90%, based on the initial total amount of β-lactone. The yield refers to the chiral yield or to the total yield.

In principle, chiral monohalogenated β-lactones for carrying out the inventive ring opening reaction are known in the art. For example, the β-lactones can be obtained by hydrochlorination of non chiral precursors with tributyltinhydride as disclosed in CH 680 588 A5.

In preferred embodiment of the invention, the chiral 4-(halomethyl)oxetane-2-ones are obtained according to a [2+2] cycloaddition reaction in the presence of a chiral catalyst. Specifically, the chiral β-lactone is obtained by a novel [2+2] cycloaddition of ketene with an aldehyde X—CH$_2$—CHO, wherein X is selected from Cl, Br and I, in the presence of a chiral catalyst.

Ketene (ethenone, formula $C_2H_2O$) is a colorless gas, which is highly reactive due to two adjacent double bonds in the molecule.

Chiral catalysts usually comprise at least one asymmetric atom. However, other chiral catalysts are known, which are chiral although not comprising a chiral C-atom, for example BINAP. They interact with the reactants in a manner such that chiral products are obtained instead of a racemate.

In a preferred embodiment of the invention, the chiral catalyst is selected from Lewis acid-Lewis base bifunctional metal catalysts and phosphine catalysts.

Preferably, the chiral catalyst is a Lewis acid-Lewis base bifunctional metal catalyst. The Lewis acid and Lewis base can either be separate compounds or can be associated with each other by ionic, covalent or other interactions, for example in a metal complex. When being separate components, the Lewis acid and Lewis base are associated with each other at least in the catalytic state in order to catalyze the enantioselective reaction. The Lewis acids are preferably metal atoms, metal ions or metal salts and the Lewis bases are chiral organic ligands, usually comprising amine, phosphine, alcohol and/or amide groups. The catalysts are bifunctional, because the chirality is a property of the ligands and thus independent from the Lewis base. Therefore, the bifunctional catalysts are distinct from chiral metal complex catalysts such as Wilkinson catalyst, in which only the overall complex, but not the ligands themselves, are chiral.

Preferably, the chiral catalyst comprises a Lewis base selected from chiral amines, chiral phosphines, chiral alcohols and chiral amides. The chiral amine is preferably an alkaloid, preferably quinine or quinidine, a triamine or salen. The chiral phosphine is preferably SEGPHOS, TUNEPHOS or BINAP. The chiral amide is preferably a bissulfonamide. The chiral catalyst may also be a derivative of any of the above.

In a preferred embodiment, the Lewis acid/Lewis base bifunctional catalyst comprises a metal atom as the Lewis acid. The Lewis acid may be provided in the form of an ion, a salt or a metal complex. One, two or more ligands may be attached to the metal to form a metal complex. In a preferred embodiment of the invention, the metal is selected from those of groups (I) and (II) of the periodic table, preferably lithium, sodium, potassium, magnesium and calcium. Further preferred are silver, gold, cobalt, aluminum, copper, nickel, chromium, iron, tin, zinc, manganese, scandium, titanium and boron.

In a preferred embodiment, the Lewis acid/Lewis base bifunctional catalyst is a chiral alkaloid in combination with a lithium salt. Preferred respective Lewis acid/Lewis base catalyst systems are disclosed by Calter (1996), Zhu et al. (2004), and Shen et al. (2006). The catalysts comprise cinchona alkaloid Lewis bases and derivatives thereof in combination with lithium perchlorate as a Lewis acid. Usually, the Lewis base and the salt are added separately into the reaction mixture. Thus the catalyst is formed in situ. According to the invention, the alkaloid is preferably a derivative of quinine or quinidine, which is substituted at the chiral 9-position with a bulky substituents. Preferably, the bulky substituents comprises between 3 and 15, more preferably between 4 and 8 carbon and/or silicium atoms. In preferred embodiments, it is selected from branched alkyl groups, such as iso-butyl and tert-butyl, and branched silyl group with alkyl and/or aryl substituents, preferably triarylsilyl groups and trialkylsilyl groups. Especially preferred is (trimethylsilyl)quinine in combination with lithium perchlorate.

A preferred group of catalysts comprises a central Al(III) atom, to which two sulfonamide groups and one additional residue, which may be an organic or inorganic residue, are attached. Thereby, the Al(III) is coordinated by the respective N-atoms of the sulfonamide groups. The sulfonamide groups may be substituted, preferably with aryl or alkyl groups. Preferably, they are linked to each other through a bridging group. Chirality is conferred to the catalyst either by chiral nitrogen atoms of the sulfonamide groups or by C-atoms of the bridging group. For example, such catalysts are described by Nelson et al., 1999.

In another preferred embodiment, the catalyst is a chiral organic phosphine. Usually, such catalysts comprise in one molecule one, two or more phosphor atoms and one or more aromatic ring systems. Amongst such phosphines, BINAPHANE ((R,R)-1,2-Bis[(R)-4,5-dihydro-3H-binaphtho(1,2-c:2',1'-e)phosphepino]benzene; CAS 253311-88-5; see scheme 2d)) is preferred, either in the R- or S-form. The development and use of BINAPHANE is disclosed by Mondal et al., 2010.

The process according to the invention may comprise an additional purification step, whereby the L-carnitine is subjected to an electrodialysis and a subsequent recrystallization treatment. Such techniques are generally known to the skilled person.

Electrodialysis (ED) is a membrane technology used to purify organic products in liquid mixtures. The ED can be used to reduce the salt concentration in a mixture in a discretionary way. The driving force for this separation is an electric field over the membranes. Pressure driven membrane processes such as Reverse Osmosis, nanofiltration, ultrafiltration or microfiltration can be applied to concentrate/retain organic compounds. The salts will only be partially concentrated/retained, depending on the type of membrane used.

The betaine (L-carnitine) can be isolated and purified using methods known in the art. An excess of tertiary amine as well as parts of the water used as solvents can be removed by distillation, preferably under reduced pressure. The excess amine may be recovered and recycled.

A salt byproduct is preferably removed by membrane technology (e.g. Electrodialysis, reverse osmosis, nanofiltration, ultrafiltration or microfiltration), advantageously after removing the volatile compounds as described above. The betaine (L-carnitine) can be isolated by conventional methods, e.g. by distilling off the water from diluate obtained after electrodialysis followed by recrystallization.

The inventive process solves the problems underlying the invention. The process is relatively simple and economic and requires only a low number of process steps. Thus side reactions are avoided and the total yield and enantiomeric yield are high. The L-carnitine can be obtained without using tin organic compounds or other toxic reactants, which would be problematic in a food and feed product. The use of precious metal catalysts is not necessary. Alternative pathways are available which provide more flexibility for carrying out the process.

Specifically, compared to the process of CH 680588 A5, the inventive process is carried out in a one-step reaction, whereas the prior art process is carried out in a two-step reaction. Further, the inventive process requires relatively low amounts of a base compared to a classical ester hydrolysis. The TMA can be recycled and reintroduced into the process. The inventive reaction can be carried out without increased temperatures and at normal pressure. In summary, the inventive process is highly efficient regarding energy, time and use of chemicals.

Another aspect of the present invention is an L-carnitine which is obtainable by a process as described supra. Said L-carnitine is characterized by possessing a unique impurity profile. Specifically, the L-carnitine according to the invention exhibits hydroxycrotonic acid as the main impurity. Preferably, the amount of hydroxycrotonic acid is equal or less than 0.1 wt-%, more preferably in the range of 0.5-0.1 wt-% and most preferably in the range of 0.5-0.005 wt-%, while other impurities are negligible.

Due to the presence of hydroxycrotonic acid as main impurity, the L-carnitine according to the invention is superior to the state of the art. Since hydroxycrotonic acid is non-toxic, non-carcinogenic and non-mutagenic (Ames-Test negative, LD50 (rat)>2000 mg/kg bw), it does not have to be removed before adding the L-carnitine into food and feed compositions.

The unique impurity profile of the L-carnitine is a direct result of the process according to the invention. It is not achievable with the two-step, state of the art processes according to e.g. U.S. Pat. No. 5,473,104 (which furthermore starts with different educts compared to the invention) or CH 680 588, since said state of the art processes are prone to resulting in a variety of different, often hazardous side products.

EXAMPLES

L-carnitine was produced from chloroethanal and ketene. The reaction pathway is shown in scheme 4 below Scheme 4: Reaction pathway of carnitine synthesis according to examples 1 and 2.

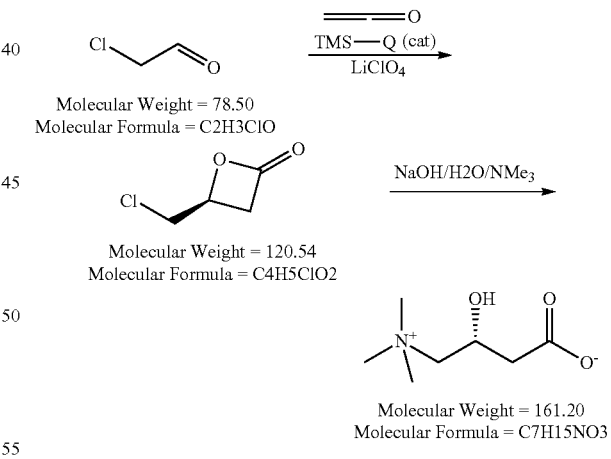

Analytical Methods:

The reaction and the ED are monitored by HPLC on a cation exchange column with UV- and conductometric detection.

Assay carnitine: HPLC, cation exchange column, UV and conductivity detection eluent: acidified water/acetonitrile, using both D- and L-carnitine as a standard.

Enantiomeric purity: the product is derivatized using a chiral, fluorescent reagent. The reaction mixture is analyzed by HPLC using an ODS-column and flourometric detection.

Example 1

Synthesis of β-Lactone

A TMSQ catalyst (see scheme 2b) above) was prepared according to the method of Michael A. Calter, J. Org. Chem. 1996, 61, 8006-8007. The catalyst was used in the following [2+2] cycloaddition reaction. In a 500 ml double jacketed reactor (equipped with over head stirrer, cryostate for cooling, nitrogen inlet; ketene dip tube) under nitrogen atmosphere, methylene chloride and a solution of a chloroacetaldehyd in methylene chloride (10.0 g dissolved in 135 g DCM) are charged. The solution is cooled to −50° C. followed by addition of 5.16 g (TMS Quinire, dissolved in 55.17 g methylene chloride) and 4.09 g $LiClO_4$ (dissolved in 54.1 g DCM and 18.0 g THF). Ketene is bubbled through the solution (7 g/h) for 2 h. The reaction is followed by inline IR (characteristical wave number of product approx 1832). The reaction is quenched with saturated aqueous bicarbonate solution (579.1 g). After separation of layers, the organic layer is dried with $MgSO_4$ and evaporated to dryness in vacuo. The crude β-lactone is used for the next step without further purification.

Example 2

Conversion of Reaction Product to L-Carnitine

The crude product is added to an aqueous solution of NaOH and TMA (water 95.0 g, NaOH 7.3 g, TMA 45% in water 20.8 g,) at 0° C. The reaction is stirred at that temperature for 1 h and warmed up to room temperature. Stirring is continued for 1 h. HPLC and IC quoted 40% conversion to carnitine (over 2 steps) with an L-carnitine assay of 85.5.

Example 3

Reaction in a Biphasic System 4-(chloromethyl)oxetane-2-one (10 wt % in organic solvent DCM or toluene) is treated with a mixture of 2.5 eq. of TMA (10-40 wt % in H2O) and 1.2-1.4 eq. of NaOH. The two-phase reaction at 0° C. followed by reaction for 1 h at room temperature yields L-carnitine (over 2 steps, dissolved in the aq. phase) in approx. 30% conversion with an L-carnitine assay of 85%. Main side product is hydroxycrotonic acid.

Example 4

Reaction without NaOH

A solution of lactone in water (50 wt %) is treated with 1.2 eq. of TMA at <−10° C. and autoclaved. The reaction mixture is heated to 90° C. HPLC and IC quoted carnitine (over 2 steps) with an L-carnitine assay of 82%. Main side product is hydroxycrotonic acid.

Example 5

Reaction at Low Temperature

An aqueous solution of sodium hydroxide (1.4 eq) and TMA (1.2 eq) is prepared and cooled to 0° C. At that temperature the β-lactone is added within 1 h. The reaction mixture is stirred further for 1 to 2 h, warmed up to room temperature and analyzed. HPLC and IC quoted 23% conversion to carnitine (over 2 steps) with an L-carnitine assay of 84.6%. Main side product is hydroxycrotonic acid.

Example 6

Reaction in an Organic Solvent 4-(chloromethyl)oxetane-2-one (10 wt % in organic solvent Ethanol) is treated with a mixture of 2.5 eq. of TMA (10-40 wt % in $H_2O$) and 1.2-1.4 eq. of NaOH. The reaction for 1 h at 0° C. followed by warming up to room temperature yields L-carnitine (over 2 steps) in approx. 22% conversion with an L-carnitine assay of 84.8%. Main side product is hydroxycrotonic acid.

Example 7

Reaction in an Organic Solvent 4-(chloromethyl)oxetane-2-one (10 wt % in organic solvent Ethanol) is added to a mixture of 2.5 eq. of TMA (10-40 wt % in $H_2O$) and 1.2-1.4 eq. of NaOH. The reaction for 1 h at 0° C. followed by warming up to room temperature yields L-carnitine (over 2 steps) in approx. 22% conversion with an L-carnitine assay of 84.8%. Main side product is hydroxycrotonic acid.

Example 8

Reaction in a Biphasic System 4-(chloromethyl)oxetane-2-one (10 wt % in organic solvent DCM or toluene) is added to a mixture of 2.5 eq. of TMA (10-40 wt % in $H_2O$) and 1.2-1.4 eq. of NaOH. The two-phase reaction at 0° C. followed by reaction for 1 h at room temperature yields L-carnitine (over 2 steps, dissolved in the aq. phase) in approx. 30% conversion with an L-carnitine assay of 85%. Main side product is hydroxycrotonic acid.

Example 9

General Procedure for Salt Removal Via ED

The setup used to carry out the ED treatments consisted of an ED miniplant equipped with a stack with 10 pairs of PES-Membranes of 64 cm2. The experiments were carried out in batch-mode; however, a continuous operation mode can be also implemented. 3 pumps were responsible to circulate the concentrate (waste water stream), dilute (product stream) and electrolyte (service stream) solutions to the membrane stack. The flux of these 3 streams was adjusted and measured with 3 rotameters. In order to guarantee a maximisation of the process yield, a control of pH and temperature in the concentrate and dilute streams was implemented. During the ED-experiments pH, electrical conductivity, temperature and flux of these 3 streams are controlled and recorded.

The above described setup was also used to desalt and purify L-carnitine from a liquid reaction mixture. The yield of L-carnitine obtained under optimized conditions was 88-94%. The diluate stream containing the product is evaporated to dryness in a rotavapor under vacuum.

Example 10

General Procedure for Recrystallization

A laboratory reactor is charged with 100 g of carnitine and 300 g of ethanol. The reactor is heated up to 65° C. and stirred until all carnitine has been dissolved. Afterwards the reactor temperature is set to 37° C. At 37° C. seed cystals of pure L-carnitine are added. The reactor temperature is cooled down to 20°. And 900 g of acetone are added within 2 hours. Afterwards the suspension is cooled down to 10° C. At 10° C. the solids are isolated and washed with acetone and dried at 55° C. and <100 mbar.

As a result, 86.1 g of a crystalline-white dry solid were obtained. The solid comprised 99% (w/w) of total carnitine and 0.03-0.01% (w/w) of hydroxycrotonic acid. The enantiomeric purity was 99.60% (e.e.). The residual solvent content was 349 mg/kg ethanol and 386 mg/kg acetone. The total yield of L-carnitine was 88.6%.

LITERATURE

Calter, Catalytic, Asymmetric Dimerization of Methylketen, J. Org. Chem. 1996, 61, 8006-8007.
Mondal et al., Phosphine-Catalyzed Asymmetric Synthesis of β-Lactones from Arylketones and Aromatic Aldehydes, 2010, Org. Lett., Received Jan. 12, 2010.
Nelson et al., Catalytic Asymmetric Acyl Halide-Aldehyde Cyclocondensations. A Strategy for Enantioselective Catalyst Cross Aldol Reactions, J. Am. Chem. Soc. 1999, 121, 9742.
Shen et al., Catalytic Asymmetric Assembly of Stereo-Defined Propionate Units: An Enantioselective Synthesis of (−)-Pironetin, J. Am. Chem. Soc. 2006, 128, 7436-7439.
Zhu et al, Cinchona Alkaloid-Lewis Acid Catalyst Systems for Enantioselective Ketene-Aldehyde Cycloadditions, J. Am. Chem. Soc. 2004, 126, 5352-5353.

The invention claimed is:

1. A process for the production of L-carnitine, wherein a β-lactone, which is a 4-(halomethyl)oxetane-2-one, is converted into carnitine with trimethylamine (TMA), wherein the β-lactone is not subjected to a hydrolysis step before being contacted with the trimethylamine.

2. The process of claim 1, wherein a basic hydrolysis and addition of trimethylamine (TMA) are carried out in one process step.

3. The process of claim 1, wherein the basic hydrolysis is carried out with a metal hydroxide, preferably sodium hydroxide.

4. The process of claim 3, wherein the β-lactone is brought into contact with the metal hydroxide and the trimethylamine essentially at the same time.

5. The process of claim 3, wherein the amount of the metal hydroxide is 1.1 to 1.6 equivalents, preferably 1.2 to 1.4 equivalents, based on the initial amount of β-lactone.

6. The process of claim 3, wherein the β-lactone is brought into contact with an aqueous solution comprising the metal hydroxide and the trimethylamine.

7. The process of claim 3, wherein a solution of the β-lactone in an organic solvent is provided and mixed with an aqueous solution comprising TMA and a metal hydroxide.

8. The process of claim 1, wherein the reaction is carried out at a temperature between −20° C. and 40° C., preferably between 0° C. and 25° C.

9. The process of claim 1, wherein basic hydrolysis is mediated by the TMA and no additional base is added for basic hydrolysis.

10. The process of claim 1, wherein the β-lactone is a chiral β-lactone and the carnitine is L-carnitine.

11. The process of claim 1, comprising an additional step, in which the L-carnitine is purified via a combination of electrodialysis and subsequent recrystallization.

12. The process of claim 1, comprising a preceding step, in which the β-lactone is obtained in a [2+2] cycloaddition of ketene with an aldehyde X—$CH_2$—CHO, wherein X is selected from Cl, Br and I, in the presence of a chiral catalyst.

13. The process of claim 12, wherein the chiral catalyst is a Lewis acid-Lewis base bifunctional metal catalyst or an organic phosphine catalyst.

14. L-carnitine, characterized by having an amount of hydroxycrotonic acid in the range of 0.5-0.1 wt-% or in the range of 0.5-0.005 wt-%.

15. The process of claim 4, wherein the amount of the metal hydroxide is 1.1 to 1.6 equivalents, preferably 1.2 to 1.4 equivalents, based on the initial amount of β-lactone.

16. The process of claim 4, wherein the β-lactone is brought into contact with an aqueous solution comprising the metal hydroxide and the trimethylamine.

17. The process of claim 5, wherein the β-lactone is brought into contact with an aqueous solution comprising the metal hydroxide and the trimethylamine.

18. The process of claim 6, wherein a solution of the β-lactone in an organic solvent is provided and mixed with an aqueous solution comprising TMA and a metal hydroxide.

19. The L-carnitine of claim 14, obtainable by a process according to claim 11.

* * * * *